(12) United States Patent
Peuchert et al.

(10) Patent No.: US 7,687,418 B2
(45) Date of Patent: Mar. 30, 2010

(54) X-RAY OPAQUE GLASS, METHOD FOR THE PRODUCTION AND USE THEREOF

(75) Inventors: Ulrich Peuchert, Bodenheim (DE); Uwe Kolberg, Mainz (DE); Joern Besinger, Landshut (DE)

(73) Assignee: Schott AG, Mainz (DE)

( * ) Notice: Subject to any disclaimer, the term of this patent is extended or adjusted under 35 U.S.C. 154(b) by 14 days.

(21) Appl. No.: 10/589,161

(22) PCT Filed: Dec. 28, 2004

(86) PCT No.: PCT/EP2004/014760

§ 371 (c)(1),
(2), (4) Date: Aug. 10, 2006

(87) PCT Pub. No.: WO2005/085147

PCT Pub. Date: Sep. 15, 2005

(65) Prior Publication Data

US 2007/0184964 A1     Aug. 9, 2007

(30) Foreign Application Priority Data

Mar. 4, 2004  (DE)  ........................ 10 2004 011 218

(51) Int. Cl.
| | |
|---|---|
| C03C 3/095 | (2006.01) |
| C03C 3/097 | (2006.01) |
| C03C 3/112 | (2006.01) |
| C03C 3/11 | (2006.01) |
| C03C 3/076 | (2006.01) |
| C03C 3/06 | (2006.01) |
| C03C 3/078 | (2006.01) |
| C03C 3/062 | (2006.01) |
| C03C 3/00 | (2006.01) |
| C09K 3/00 | (2006.01) |

(52) U.S. Cl. ............................. 501/64; 106/35; 501/54; 501/55; 501/56; 501/57; 501/63; 501/72; 501/73

(58) Field of Classification Search .................. 501/21, 501/64, 72, 54–57, 63, 73; 106/35
See application file for complete search history.

(56) References Cited

U.S. PATENT DOCUMENTS

| | | | |
|---|---|---|---|
| 5,641,347 A | 6/1997 | Grabowski et al. | |
| 6,128,430 A * | 10/2000 | Chu et al. | 385/142 |
| 6,297,181 B1 * | 10/2001 | Kunert et al. | 501/57 |
| 6,577,667 B1 | 6/2003 | Romer et al. | |
| 6,627,569 B1 | 9/2003 | Naumann et al. | |
| 6,630,420 B1 | 10/2003 | Naumann et al. | |
| 6,800,574 B2 * | 10/2004 | Anderson | 501/33 |
| 6,817,212 B1 | 11/2004 | Roemer et al. | |
| 2003/0137230 A1 | 7/2003 | Martin et al. | |
| 2004/0079258 A1 | 4/2004 | Hoescheler et al. | |
| 2004/0116550 A1 | 6/2004 | Hoescheler et al. | |
| 2005/0039492 A1 | 2/2005 | Roemer et al. | |
| 2005/0109062 A1 | 5/2005 | Stelle et al. | |

FOREIGN PATENT DOCUMENTS

| | | |
|---|---|---|
| DE | 32 06 227 | 9/1983 |
| DE | 41 00 604 | 2/1992 |
| DE | 198 49 388 | 5/2000 |
| DE | 199 06 240 | 8/2000 |
| DE | 199 45 517 | 8/2000 |
| DE | 100 63 939 | 7/2002 |
| DE | 101 00 680 | 7/2002 |
| DE | 103 48 466 | 5/2005 |
| EP | 0 716 049 | 6/1996 |
| EP | 1 357 883 | 11/2003 |
| GB | 2 251 814 | 7/1992 |
| WO | 98/58884 | 12/1998 |
| WO | 01/14264 | 3/2001 |
| WO | 01/14265 | 3/2001 |
| WO | 02/49581 | 6/2002 |
| WO | 02/055028 | 7/2002 |
| WO | 03/031355 | 4/2003 |

OTHER PUBLICATIONS

Masayuki Nogami: "Glass Preparations of the . . . " Journal of Non-Crystalline Solids 69, 1985, pp. 415-423 (in English).

* cited by examiner

*Primary Examiner*—David M. Brunsman
*Assistant Examiner*—Kevin M Johnson
(74) *Attorney, Agent, or Firm*—Michael J. Striker

(57) ABSTRACT

The X-ray opaque glass is characterized by a composition, in mol %, of $SiO_2$, 75-98; $Yb_2O_3$, 0.1 to 40; and $ZrO_2$, 0 to 40. Preferred embodiments of the glass are free of $Al_2O_3$ and $B_2O_3$. The glass is produced from the glass batch by melting at a temperature of at least 1500° C. in an iridium or iridium alloy vessel with the assistance of high-frequency radiation. In preferred embodiments of the glass production process at least one raw material ingredient is present in the batch as a nanoscale powder. The glass is useful in dental applications, optical applications, and biomedical applications, or for photovoltaics, or as a target material in PVD processes.

44 Claims, No Drawings

X-RAY OPAQUE GLASS, METHOD FOR THE PRODUCTION AND USE THEREOF

BACKGROUND OF THE INVENTION

The invention relates to an X-ray opaque glass, to a process for producing it and to its use.

Plastic dental compositions are increasingly being used for dental restoration in the dental sector. These plastic dental compositions usually comprise a matrix of organic resins and various inorganic fillers. The organic fillers predominantly comprise powders of glasses, (glass-)ceramics, quartz or other crystalline substances (e.g. $YbF_3$), sol-gel materials or Aerosils.

The use of plastic dental compositions is intended to avoid possible harmful side-effects of amalgam and to achieve an improved aesthetic impression. Depending on the plastic dental compositions selected, they can be used for different dental restoration measures, for example for tooth fillings and also for securing parts, such as crowns, bridges and inlays.

The filling material per se is intended to minimize the shrinkage caused by the polymerization of the resin matrix during curing. For example, if there is a strong adhesion between tooth wall and filling, excessive polymerization shrinkage can lead to the tooth wall breaking. If the adhesion is inadequate, excessive polymerization shrinkage may result in the formation of peripheral gaps between tooth wall and filling, which can promote secondary caries. Furthermore, certain physical and chemical demands are imposed on the fillers:

It must be possible to process the filling material to form powders that are as fine as possible. The finer the powder, the more homogenous the appearance of the filling. At the same time, the polishing properties of the filling are improved, which in addition to reducing the surface area available for attack also leads to improved resistance to abrasion and therefore to a longer-lasting filling. To enable the powders to be processed successfully, it is also desirable for the powders not to agglomerate. This undesirable effect occurs in particular with filling materials produced with the aid of sol-gel processes.

Furthermore, it is advantageous if the filler is coated with functionalized silane, since this facilitates formulation of the dental composition and improves the mechanical properties.

Furthermore, the refractive index and color of the plastic dental composition and therefore also of the filler should be as well matched as possible to the natural tooth material, so that it is as far as possible indistinguishable from the surrounding, healthy tooth material. The grain size of the pulverized filler being as small as possible also plays a role in this aesthetic criterion.

It is also important for the thermal expansion of the plastic dental composition in the range of use, i.e. usually between −30° C. and +70° C., to be matched to that of the natural tooth material, in order to ensure that the dental restoration measure is sufficiently able to withstand temperature changes. An excessively high stress caused by temperature changes can likewise give rise to the formation of gaps between the plastic dental compositions and the surrounding tooth material, which in turn can form preferred points of attack for secondary caries. In general, fillers with the lowest possible coefficient of thermal expansion are used, in order to compensate for the high thermal expansion of the resin matrix.

A good chemical resistance of the fillers with respect to acids, alkalis and water and good mechanical stability under load, such as for example during the movement produced by chewing, can also contribute to a long service life for the dental restoration measures.

Furthermore, for the treatment of patients, it is imperative that dental restoration measures can be seen in an X-ray image. Since the resin matrix itself is generally invisible in an X-ray image, the fillers have to provide the required X-ray absorption. A filler of this type which provides sufficient absorption of X-radiation is described as X-ray opaque. Constituents of the filler, for example certain components of a glass, or additional substances, known as X-ray opacifiers, are generally responsible for the X-ray opacity. A standard X-ray opacifier is $YbF_3$, which can be added to the filler in crystalline, milled form.

Because the plastic dental composition in use is usually introduced into cavities from cartridges and is then modeled in the cavities, it is often supposed to be thixotropic in the uncured state. This means that its viscosity decreases when pressure is exerted, whereas it is dimensionally stable without the action of pressure.

Among plastic dental compositions, a distinction also needs to be drawn between dental cements and composites. In the case of dental cements, also known as glass ionomer cements, the chemical reaction of the fillers with the resin matrix leads to curing of the dental composition, and consequently the curing properties of the dental composition and therefore their workability is influenced by the reactivity of the fillers. This often involves a setting process which is preceded by a radical surface curing, for example under the action of UV light. Composites, also referred to as filling composites, contain, by contrast, fillers which are as chemically inert as possible, since their curing properties are determined by constituents of the resin matrix itself and a chemical reaction of the fillers is often disruptive for this.

Because glasses, on account of their different compositions, represent a class of materials with a wide range of properties, they are often used as fillers for dental compositions. Glasses of this type are generally known as dental glasses. Reactive dental glasses for use in dental cements are known, for example, from DE 100 63 939 A1.

Chemically inert dental glasses for use as filler in composites form the subject matter of DE 198 49 388 A1. The glasses proposed therein must contain significant proportions of $Al_2O_3$, ZnO, F and $Na_2O$, which has an adverse effect on their chemical resistance. Furthermore, the F, ZnO and $Na_2O$ contents can lead to reactions with the resin matrix, which can in turn have effects on their polymerization properties. In the glasses which form the basis of DE 198 49 388 A1, $ZrO_2$ must also be present as a further constituent in order to effect X-ray opacity. Fillers of this type are too reactive in particular for the most modern epoxy-based dental compositions, in which excessively rapid, uncontrolled curing may occur.

DE 101 00 680 A1 has disclosed dental glasses which contain at least two components. These binary glass systems comprise a high content of $SiO_2$ and $HfO_2$, $TaO_5$, $ZrO_2$ or $La_2O_3$, which effect the X-ray opacity. However, only the binary glasses comprising $SiO_2$ and $HfO_2$ or $SiO_2$ and $Ta_2O_5$ were produced by a melting process, whereas the glasses comprising $SiO_2$ and $ZrO_2$ and/or $La_2O_3$ were obtained with the aid of a sol-gel process. The sol-gel process has been described, for example, by Nogami in Journal of Non-Crystalline Solids, 96 (1985) 415-423.

In economic terms, it has the drawback of being too expensive for the production of relatively large quantities of dental glasses. Furthermore, glasses produced by the sol-gel process generally contain a large amount of water, making it difficult to process them further to form powders. In particular, sol-gel glass powders are often prone to agglomeration. Furthermore, DE 101 00 680 A1 proposes ternary glass systems which, in addition to $SiO_2$ as the main constituent, also contain $ZrO_2$ as X-ray opaque constituent and $La_2O_3$, $HfO_2$, $Y_2O_3$, $TiO_2$ and $Al_2O_3$ as further constituents. The ternary system comprising $SiO_2$, $La_2O_3$ and $B_2O_3$ is also described.

SUMMARY OF THE INVENTION

These dental glasses have the drawback that in terms of their X-ray opacity, their processing properties, their refractive index and their production process, they are not optimally suited to all applications as a dental glass. Therefore, it is an object of the present invention to provide an X-ray opaque glass which is suitable as a relatively unreactive filler for composites and, in particular on account of being relatively unreactive, makes a contribution to the long-term stability of the latest generation of fillers based on epoxy resin. These glasses are also to allow the inexpensive production of dental compositions which make do without expensive, crystallized X-ray opacifiers and without filling cement based on acrylate. A further object of the invention is to provide an economic process for producing the abovementioned glasses.

The glass according to the invention contains 60-98 mol % $SiO_2$, 0.1-40 mol % $Yb_2O_3$ and does not contain any $Al_2O_3$ and/or $B_2O_3$. It has been found that a surprisingly good X-ray opacity is achieved as a result of the $Yb_2O_3$ content, and the refractive indexes of these glasses can be very closely matched to the natural tooth appearance. The glass according to the invention may also contain up to 40 mol % $ZrO_2$.

It is preferable for the glass according to the invention, in addition to 60-98 mol % $SiO_2$ and 0.1-40 mol % $Yb_2O_3$, to contain additionally 0.1-40 mol % $ZrO_2$. The addition of this third component stabilizes the glass, so that it is less prone to crystallization. Crystallization of a glass needs to be avoided, since it would inter alia influence the optical properties in such a way that the filling material would be difficult if not impossible to match to the natural composition.

In a further preferred embodiment, in addition to 70-98 mol % $SiO_2$ and 0.5-15 mol % $Yb_2O_3$, the glass according to the invention also contains 0.5-15 mol % $ZrO_2$. Particularly preferred ranges are 70-98 mol % $SiO_2$, 1-15 mol % $Yb_2O_3$ and additionally 1-15 mol % $ZrO_2$.

In a very particularly preferred embodiment, the glass according to the invention contains, as additional components, $WO_3$, $La_2O_3$, $Nb_2O_5$, $HfO_2$, $Ta_2O_5$, $Gd_2O_3$, $Lu_2O_3$, $Sc_2O_3$, $Y_2O_3$, in each case in an amount of up to 40 mol %, and/or $F_2$ in an amount of up to 5 mol %. The $F_2$ content can be obtained by adding $YbF_3$ to the batch, in which context a person skilled in the art will know that fluorine in a glass is not in the form of a gaseous component. By combining the oxides of these additional heavy elements, the X-ray absorption spectrum of the glass according to the invention, which is formed by superposing the X-ray absorption spectra of the individual components, can be matched to the emission spectrum of different X-ray sources. It is in this way possible to ensure that lower radiation doses are required for the examination of patients.

To improve the melting properties of the glasses with the aid of high-frequency processes (cf. below), the glass according to the invention may also contain in each case up to 10 mol % of the alkali metal oxides $Li_2O$, $Na_2O$ and/or $K_2O$, the total content of which should be at most 10 mol %.

In a preferred embodiment, the glasses according to the invention contain the alkaline-earth metal oxides MgO, CaO, SrO, BaO and/or ZnO in each case up to an amount of 10 mol %, the total quantity of which should in turn be at most 10 mol %. The alkaline-earth metal oxides promote the melting properties and the glass formation and reduce the susceptibility to crystallization. Furthermore, ZnO, SrO and BaO can have an antibacterial action and improve the X-ray opacity.

It has been found that despite the content of alkali metal and/or alkaline-earth metal oxides in the $SiO_2$—$Yb_2O_3$ matrix of the glass according to the invention, the chemical resistance of this glass is surprisingly good, and consequently an unreactive nature in conjunction with the resin matrix and therefore a very long service life of the overall dental composition is likely. It is of course also possible for the color appearance of the glass to be adapted by the addition of customary oxides.

As additional components, which can improve certain glass properties, such as the susceptibility to crystallization, melting properties, etc., it is provided that the glass according to the invention may contain in each case up to 10 mol % $TiO_2$, $GeO_2$ and/or $P_2O_5$, the total content of which should be at most 15 mol %.

Restricting the number of components allows the probability of impurities contaminating the glass to be reduced. Therefore, the glass according to the invention for particular applications may preferably contain only at most five of the abovementioned oxidic components. An even higher purity can be achieved by restricting the choice of oxidic components to at most four and particularly preferably at most three.

The invention also comprises glass powders made from the abovementioned glasses. The glass powders are produced by known processes, for example as described in DE 41 00 604 C1. The glass powder according to the invention preferably has a mean grain size of up to 20 µm. A mean grain size of 0.2 µm can be set as the lower limit, although the invention of course also encompasses smaller grain sizes. The abovementioned glass powder can serve as starting material for the use of the glasses according to the invention as fillers.

In a preferred embodiment, the surface of the glass powder is silanized using the conventional methods. The silanization allows the bonding of the inorganic fillers to the plastic matrix of the dental composition to be improved.

The glass according to the invention has a very high melting point and cannot be produced by conventional melting processes. Therefore, the subject matter of the invention also encompasses the provision of a melting process which can be employed for the glass. Melting processes for producing glasses generally include the step of batch preparation, during which the raw material components are mixed, pretreated, purified, etc., according to requirements, the step of batch charge, in which the prepared raw material components are introduced into the melting vessel, and the actual melting. Other processes, such as for example sol-gel processes, cannot be used economically to produce relatively large quantities of glass. Moreover, there is a risk of powder agglomeration in particular in the case of glasses which include $SiO_2$ and $ZrO_2$ and have been produced using sol-gel processes. One process according to the invention is high-temperature melting. The temperature of the glass melt is in this case at least 1500° C., preferably at least 1600° C.

The temperatures which occur during high-temperature melting place particular demands on the materials used for the melting vessel. In one preferred embodiment, therefore, the melting vessel at least partially comprises solid iridium and/or an alloy with a high iridium content. Iridium contents of at least 95% have proven suitable for alloys of this type. On account of the high oxidation sensitivity of iridium, an apparatus which includes such components must at least in part be purged with a suitable shielding gas. The heating of the melting vessel during high-temperature melting can be carried out using conventional methods, for example by means of inductive heating with a frequency of approximately 8 kHz to approximately 12 kHz. A method of this type and an apparatus for carrying out the method are described extensively for other glass systems in DE 103 48 466 (not yet published), the content of disclosure of which is hereby incorporated in full in the present document.

In another preferred process, the high temperatures during the melting operation are generated by introducing high-frequency alternating electromagnetic fields into a glass batch which has already been at least partially liquefied. The frequency range may usually be between 50 kHz and 2 MHz. This process is known as high-frequency melting. Processes of this type and corresponding apparatuses are described in detail for example in WO 01/14264 A1, WO 01/14265 A1 and WO 03/031355 A1. The content of disclosure of these documents is hereby likewise incorporated in its entirety in the present document. However, since the mechanism on which high-frequency melting is based only takes effect above a certain temperature, it is customary for heating using conventional heating methods, for example using burners, to take place before the alternating field is switched on.

In principle temperatures of any desired level can be achieved by high-frequency melting. Up to 2500° C. can already be reached using commercially available laboratory equipment. Even higher temperatures can be realized by suitable modifications. High-temperature melting may preferably be used, since it has been found that the oxygen ion conductors $Yb_2O_3$ and $ZrO_2$ as pure substances can be excellently coupled to the alternating electromagnetic field. When other substances such as $SiO_2$ which are nonconductive are admixed, the conductivity decreases with increasing concentration until the melt is no longer coupled. This composition point is not precisely defined, but rather depends on apparatus variables and the time curve of the temperature profile of the melt. In order to allow even compositions with a high $SiO_2$ content to be melted with the aid of high-frequency radiation, it has proven appropriate to add small quantities of alkali metal oxides, preferably $Li_2O$ and $Na_2O$ up to 10 mol %. Even in low concentrations, these oxides increase the conductivity and therefore the high-frequency meltability greatly.

The frequency of the alternating electromagnetic field during high-frequency melting is dependent on the volume to be melted. During the high-frequency melting, it may preferably be from 50 kHz to 2 MHz. Alternatively, it is possible to use processes such as plasma melting, laser melting or mirror furnace technology.

Alternative processes to the high-temperature melting described here also include flame hydrolysis, in which gaseous precursors are used, or plasma spraying, in which powders are usually used as precursors.

The glass according to the invention primarily comprises high-melting raw materials, which as in the case of $SiO_2$, $Yb_2O_3$ and $ZrO_2$ are relatively coarse-grained and unreactive in the delivered state. These can be melted in the usual way, i.e. by mixing the pulverulent, commercially available starting oxides and charging them into the melting vessel. On account of the unreactive nature and high melting temperatures of the starting oxides and the high viscosity of the glass which is formed, kinematic delays may lead to the melting process progressing very slowly. In other words, although the temperature would in principle be high enough to melt a desired glass composition close to the eutectic of the starting components, it would not be high enough for the starting oxides themselves. Therefore, in this case it is very much solid substances which are present, and these only react with one another gradually by way of very slow solid-solid reaction processes. In this case, the glass formation progresses only slowly, since mass transfer has to take place over relatively long distances. To achieve reaction rates which are economically viable for glass production, the temperature has to be raised to well above the level which is thermodynamically necessary. This is often disadvantageous and/or impossible for reasons of energy economics and/or apparatus however. Furthermore, in the size range corresponding to the previous grain size dimensions, the melt has inhomogeneities of concentration which are only eliminated slowly even with stirring.

It has been found that the melting-down operation can take place more economically—i.e. with less energy and more quickly—if at least one of the raw material components of the glass according to the invention is in nanoscale or water-soluble form. The term nanoscale is to be understood as meaning powders with very small grain sizes, usually from 10 nm to 200 nm. The at least one nanoscale raw material component can be charged into the melting vessel as batch together with the other, optionally milled raw material components.

However, it is preferable for the raw material components to be pretreated in the batch preparation, as described below, to form what are known as green bodies or green body powders. Preparing the raw material components to form a green body significantly accelerates the solid-state reactions during charging into the melting vessel, since the diffusion distances are smaller by more than an order of magnitude than if a green body were not used during batch charging. Furthermore, nanoscale raw material components have a more favorable ratio of reactive surface area to unreactive volume. The reactions take place significantly more quickly, or for a comparable reaction rate the temperature can be selected to be about 500° C. to 700° C. lower. As a result, some glass compositions can for the first time actually be melted on an industrial scale. Furthermore, in this case the abovementioned concentration inhomogeneities are not in the µm range, but rather in the range of a few nm (for example about 10 nm), so that the stirring processes for homogenization also take place significantly more quickly and more effectively.

The abovementioned green bodies can be produced in various ways. It is preferable first of all to dissolve the soluble components in a commercially available dissolver, which in principle represents a stirring mechanism with a high rotational speed, special stirring tools with high shearing forces and temperature control devices, in a predetermined quantity of a solvent, for example water. Then, the nanoscale component, for example $SiO_2$, is added in the form of powder or a prefabricated suspension, with vigorous stirring. The addition of the other, preferably nanoscale or alternatively large-crystal substances then takes place. The temperature is advantageously kept as low as possible. If heat of reaction is produced, this can be dissipated by a cooling apparatus. The stirring speed and stirring time to achieve a component distribution which is as homogenous as possible depend on the type of chemical composition of the mass and the grain sizes which can be obtained. The free-flowing to pasty suspension obtained is poured and/or spread into molds of a suitable size.

The material in the molds can then be dried. Standard drying cabinets or chamber furnaces are suitable for this purpose. However, the drying particularly preferably takes place in microwave drying installations, in which case a temperature range from 100° C. to 250° C. is preferably selected. Higher temperatures are theoretically possible but can lead to caking. It has been found that a sufficient quantity of dried green bodies is obtained in very short drying times by using a microwave installation for the drying. Furthermore, segregations caused by entrainment effects in the solvent which conventionally diffuses to the surface are avoided. Very surprisingly, it has also been ascertained that the microwave drying leads to fewer gas inclusions and therefore fewer undesirable bubbles during melting-down of the green body and/or of the green body powder.

In a preferred configuration of the method, the mold into which the suspension is introduced and the green body is dried at least partially comprises a non-wetting material. In this context, it is preferable to use TEFLON®, i.e. a fluoropolymer. As a result of this material being selected, the drying temperature is restricted to an upper limit of approximately 250° C. to 300° C. Furthermore TEFLON® is as far as possible chemically inert with respect to the material being dried. This makes it possible to avoid contamination. It has been found that if non-wetting material is used in the mold, the green body can very successfully be removed from the mold. In the case of drying vessels made from glass or metal, the desired high reactivity of the green body can lead to attacks on the mold, which on the one hand can lead to impurities and on the other hand can lead to solid caking between green body and mold, so that the green body can no longer be removed from the mold, or can only be removed with difficulty.

After drying has taken place, the green bodies can be placed into the melting vessel either as a single entity, as coarse fragments or in milled form to form part of the batch.

To further increase the homogeneity of the batch, however, the green body can also be milled again, dispersed and then the entire process described thus far for production of a green body can be repeated. The green body which is then prepared once again is known as a compact body. During milling, it is also possible to add cullet from earlier melts for reuse.

When producing the green and/or compact bodies, it is generally advantageous to add alkali metal hydroxides and therefore to work in a basic medium, i.e. generally using an alkali metal lye. In this case, dissolution and reagglomeration processes of the nanoscale $SiO_2$ and/or of the remaining solid nanoscale substances and the precipitation of water-soluble compounds as hydroxide lead to mixing of the components at a virtually monomolecular level. In this way, the original grain boundaries disappear, as it were, resulting in a very uniform green body which is easy to sinter and melt and has good setting properties. As a result, however, the glass is no longer free of alkali metals. The user must decide according to circumstances whether the benefit of significantly improved process sequences compensates for the generally minor deterioration in the chemical resistance. The use of alkali metal oxides is advantageous in particular if the actual melting operation takes place under high-frequency melting, since the alkali metal oxides, as described above, can improve the coupling capacity of the melt.

As an alternative to alkali metal oxides, it is also possible to use an aqueous ammonia solution. However, the pH is by no means as basic as in the case of alkali metal oxides, in which case the reactions described above then take place in less pronounced form. Furthermore, nitrogen may remain in the glass, for example in nitride form. It is necessary to consider for each individual case according to the particular application whether these quantities, albeit small, may be disruptive, for example by causing discoloration.

It is also possible for the green or compact bodies not to be placed directly into the melting vessel, but rather to be subjected to sintering. This can take place for example in chamber furnaces, tunnel furnaces or rotary tubular furnaces at temperatures between 700° C. and 1600° C., which has the advantage that the green or compact bodies are compacted to form sintered bodies. If a sintered body is introduced for melting, this can have the advantage of improving the heat transfer in the melt and therefore the melting properties. Furthermore, the sintering effects a volume compacting and therefore requires less space in storage, and also improves the chemical stability of the material to be stored. Furthermore, a sintered body contains fewer included gases, and less dust is produced when it is used for batch charge than when using powders. If the batch contains carbonates and/or nitrates, sintering is advantageous, because these components, when heated, tend to release gases. In particular nitrates, however, may attack the melting vessel. If the green or compact bodies are sintered, the release of gases takes place as early as during sintering, and consequently the proportion of the gas-releasing components in the batch is reduced and the sintered body can be stored for a longer time than a green or compact body. This can give rise to production engineering benefits. Furthermore, the generally expensive melting vessel in which very high temperatures have to be reached can be relieved of preliminary reactions if sintered bodies are used as batch charge, since these preliminary reactions have already taken place during the sintering. Moreover, the melting vessel can in this way be protected from the abovementioned harmful substances, for example nitrates. Consequently, it thus becomes possible to use less expensive melting vessels.

In one particularly preferred configuration of the process, the sintering takes place immediately before batch charging into the melting vessel. In a corresponding melting installation, the sintering device is directly in line before the melting device. The waste heat from the melting device can in this way during the sintering operation contribute to the preheating of the green or compact bodies to reaction temperature, and consequently the heat content of the sintered body is not lost during batch charging into the melting vessel.

The glass according to the invention can be used as dental glass. It is preferably employed as a filler in composites for dental restoration, particularly preferably for fillers based on epoxy resin which require substantially chemically inert fillers. It is also within the scope of the invention for the glass according to the invention to be used as an X-ray opacifier in dental compositions. The glass is suitable for replacing expensive crystalline X-ray opacifiers, such as for example $YbF_3$.

On account of its optical properties, the glass according to the invention can also be used for optical applications. Since it is substantially chemically inert, it is suitable for applications in display technology, as substrate glass in photovoltaics and as substrate glass for biochemical applications, in particular for molecular screening processes. On account of its high thermal stability, the glass according to the invention is also suitable as lamp glass, in particular for use in halogen lamps. Furthermore, the glass according to the invention can be used as target material for physical vapor deposition processes, known as PVD processes for short. One example of a PVD process is electron beam physical vapor deposition. In this case, the glass according to the invention, as a target in a vacuum chamber, is bombarded with an electron beam and thereby vaporized. The vapor can be deposited on a substrate so as to coat the latter.

It is also possible for the glass according to the invention to be used as starting material for glass fibers. On account of its good chemical resistance, a recommended application area is in particular the use of these glass fibers as reinforcements in composite materials and/or as reinforcements for concrete.

EXAMPLES

Examples of the glasses according to the invention are listed in Table 1. Example No. 38 is a glass which is known from DE 101 00 680 A1, which in that document was produced using a sol-gel process and is in this case produced by high-temperature melting. Example No. 37 is likewise a binary glass comprising the components $SiO_2$ and $ZrO_2$, which has been produced by high-temperature melting. Examples No. 37 and 38 serve as comparison examples for the glasses according to the invention No. 1 to 36.

To produce the glass, either green or sintered bodies were charged into the melting vessel. The melting vessel used was a crucible which predominantly comprises iridium and was heated by means of inductively supplied electrical energy. The crucible, which predominantly comprises iridium, releases the electrical energy which it takes up to the charged batch and/or the melt by means of radiant heat and direct heat conduction. The maximum melting temperature reached was about 2300° C.

For further processing, the liquid glass was removed from the melt and allowed to solidify in the form of glass gobs. The cooled glass gobs were milled, with the aid of the process known from DE 41 00 604 C1, to form a glass powder with a mean grain size of at most 10 µm. The glass properties were determined on the basis of glass gobs which had not been milled into powders. All the glasses No. 1 to 36 have an excellent chemical resistance with respect to acids, alkalis and water; furthermore, they are as chemically inert as possible. The refractive indexes $n_d$ and the density D of the variants of the glass according to the invention are likewise listed in Table 1.

Comparison Examples No. 37 and 38 contain only $SiO_2$ and $ZrO_2$, have a refractive index $n_d$ of 1.498 and 1.513, respectively, and a density D of 2.297 g/cm$^3$ and 2.357 g/cm$^3$, respectively.

By comparison, in Example No. 9, 2 mol % of the $ZrO_2$ content of Example No. 37 were substituted by $Yb_2O_3$. This substitution causes only a very minor change in the refractive index but increases the density by about 6%. Since the density correlates to the X-ray opacity, a high density at the same time means a high X-ray opacity, which is a precondition for glasses to be used as filler in dental compositions. The glass of Example No. 9 consequently improves the X-ray opacity compared to the prior art, without significantly altering the optical properties.

In Example No. 8, by comparison with Example No. 37 the $SiO_2$ content was reduced by 1.8 mol % and the $ZrO_2$ content was reduced by 3.2 mol %, whereas the glass contained 5 mol % $Yb_2O_3$. As a result, an increase in the refractive index of only around 1.7% is observed, whereas the density increases by around 17% compared with Example No. 37. Therefore, the glass of Example No. 8 is also eminently suitable for the purpose of the invention.

The ratio of the percentage increase in the density of an example glass to the percentage increase in the refractive index of an example glass, in each case with respect to the glass of Example No. 37, is referred to below as the "opacity factor" $F_0$. The higher $F_0$ is for a glass according to the invention, generally the more favorable the ratio between the change in refractive index and the increase in density achieved becomes.

Examples No. 23 to 28 demonstrate that a reduction in the $SiO_2$ content to 92 mol % and in the $ZrO_2$ content to 3 mol %, with a content of additional oxides of 4.9 mol % in the presence of $Yb_2O_3$, likewise leads to an increase in density. However, in the case of $Nb_2O_5$ and $Ta_2O_5$, the refractive index also increases greatly. Example No. 9, with an opacity factor of 17.0, demonstrates a very good compromise between the increase in refractive index and the increase in density. Furthermore, Example No. 9, by comparison with Examples No. 23 to 28, which have a considerably lower $Yb_2O_3$ content than Example No. 9 and $F_0$ values between 2.2 and 13.0, demonstrates that in particular $Yb_2O_3$ as a constituent of a glass leads to an efficient increase in the density and therefore the X-ray opacity without an excessive increase in the refractive index.

To allow the effects of the presence of $Yb_2O_3$ in glass compositions to be illustrated further, the glasses in accordance with Examples No. 1 and 2 were melted. These comprise only $SiO_2$ and a relatively high $Yb_2O_3$ content. The $Yb_2O_3$ content of 18 mol % in Example No. 1, compared to Example No. 37, brings about an increase in the refractive index of 8.6%, whereas the density rises by 64.4%. A glass with a $Yb_2O_3$ content of 25 mol % as per Example No. 2 has a refractive index which is 12.7% higher but a density which is 89.7% higher than the glass of Example No. 37. It can be demonstrated that $Yb_2O_3$ is better suited than $ZrO_2$ if the aim is the maximum possible increase in density combined with the lowest possible increase in refractive index in a glass by comparing the abovementioned examples with Examples No. 3 and 4. In Example No. 3, half the $Yb_2O_3$ content of Example No. 1 was replaced by $ZrO_2$. Although glass No. 3 obtained only has an increase in $n_d$ of 7.5% compared to Example No. 37, which would inherently be more favorable, its rise in density is also only 41.4% compared to Example No. 37. This results in the $F_0$ value of 5.6 for Example No. 3, which is significantly lower than the $F_0$ value of 7.5 in Example No. 1. Similarly, in Example No. 4, half the $Yb_2O_3$ content of Example No. 2 is replaced by ZrO. Whereas Example No. 2 has a $F_0$ value of 7.1, Example No. 4 only achieves a $F_0$ value of 5.2. Of course, the value of $F_0$ alone is not the only determining factor for possible application areas for the glasses according to the invention, since the absolute magnitude of the refractive index may also play a role.

The fact that a suitable combination also of the other constituents of the glasses according to the invention can be used to obtain a highly X-ray opaque glass with a low refractive index which is optimally suited to a range of applications and conditions can be demonstrated in particular by Examples No. 29 to 34. In addition to 92 mol % $SiO_2$, 2 mol % $Yb_2O_3$ and 3 mol % $ZrO_2$, these glasses in each case also contain one more of the abovementioned oxides. The refractive indexes of these glasses are between 1.515 and 1.553, and their density is between 2.507 g/cm$^3$ and 2.937 g/cm$^3$, resulting in $F_0$ values of between 3.5 and 11.5.

Examples 35 and 36 show a glass which, similarly to the known X-ray opacifiers, contains fluoride. For reasons of comparability with the remaining examples, the equivalent synthesis values for $La_2F_6$ and $Yb_2F_6$ are given. Example No. 35 is derived from Examples No. 29 to 34, with the additional oxidic component replaced by $La_2F_6$ (equivalent synthesis value). Compared to Comparison Example No. 37, the refractive index in this example is increased by around 1.4%, whereas the density increases by around 13.4%. $F_0$ in Example No. 35 is therefore about 9.8.

In Example No. 36, the $Yb_2O_3$ content of Example No. 9 was replaced by $Yb_2F_6$ (equivalent synthesis value). The refractive index of this glass is only 0.2% greater than that of Comparison Example No. 37, whereas the density is 5.3% higher. This results in a $F_0$ factor of around 22.8. The use of ytterbium fluoride in the glass according to the invention is therefore particularly advantageous if, when used as filler in composites for dental restoration, high demands are imposed on the optical properties of the glass.

All the examples also demonstrate that in addition to the setting of refractive index and density, it is possible to match the glass to the X-ray source by adjusting the constituents with regard to their X-ray absorption bands as described above.

Compared to the prior art, the glass according to the invention is as far as possible chemically inert, inter alia on account of the absence of $B_2O_3$ and/or $Al_2O_3$. It has an improved X-ray opacity, and its refractive indexes can be adapted to the intended application within an appropriate range around 1.498. As a result, it can advantageously be used in particular as fillers in dental compositions but also for other applications which impose high demands inter alia on the purity and also the chemical resistance and thermal stability. It can be produced on a large industrial scale at low cost by means of the process according to the invention.

TABLE 1

Compositions of the X-ray opaque glass in mol %

| | Example No. | | | | | | | | | |
|---|---|---|---|---|---|---|---|---|---|---|
| | 1 | 2 | 3 | 4 | 5 | 6 | 7 | 8 | 9 | 10 |
| $SiO_2$ | 82 | 75 | 82 | 75 | 75 | 88.1 | 88.1 | 92 | 93.8 | 88.1 |
| $Yb_2O_3$ | 18 | 25 | 9 | 12.5 | 12.5 | 5 | 10 | 5 | 2 | 0.1 |
| $ZrO_2$ | | | 9 | 12.5 | 6.25 | 6.9 | 1.9 | 3 | 4.2 | 6.9 |
| $Nb_2O_5$ | | | | | | | | | | 4.9 |
| $Ta_2O_5$ | | | | | | | | | | |
| $HfO_2$ | | | | | | | | | | |
| $WO_3$ | | | | | | | | | | |
| $La_2O_3$ | | | | | 6.25 | | | | | |
| $Y_2O_3$ | | | | | | | | | | |
| $La_2F_6$ | | | | | | | | | | |
| $Yb_2F_6$ | | | | | | | | | | |
| $n_d$ | 1.626 | 1.687 | 1.609 | 1.668 | 1.672 | 1.581 | 1.591 | 1.524 | 1.503 | 1.631 |
| D | 3.777 | 4.357 | 3.247 | 3.667 | 3.797 | 3.044 | 3.364 | 2.687 | 2.428 | 2.894 |
| $F_o$ | 7.5 | 7.1 | 5.6 | 5.2 | 5.6 | 5.8 | 7.4 | 9.6 | 17.0 | 2.9 |

| | Example No. | | | | | | | | | |
|---|---|---|---|---|---|---|---|---|---|---|
| | 11 | 12 | 13 | 14 | 15 | 16 | 17 | 18 | 19 | 20 |
| $SiO_2$ | 88.1 | 88.1 | 88.1 | 88.1 | 88.1 | 82 | 88.1 | 88.1 | 88.1 | 88.1 |
| $Yb_2O_3$ | 0.1 | 0.1 | 0.1 | 0.1 | 0.1 | 6 | 0.1 | 0.1 | 0.1 | 0.1 |
| $ZrO_2$ | 6.9 | 6.9 | 6.9 | 6.9 | 6.9 | 6 | 1.9 | 1.9 | 1.9 | 1.9 |
| $Nb_2O_5$ | | | | | | | 9.9 | | | |
| $Ta_2O_5$ | 4.9 | | | | | | | 9.9 | | |
| $HfO_2$ | | 4.9 | | | | | | | 9.9 | |
| $WO_3$ | | | 4.9 | | | | | | | 9.9 |
| $La_2O_3$ | | | | 4.9 | | | | | | |
| $Y_2O_3$ | | | | | 4.9 | 6 | | | | |
| $La_2F_6$ | | | | | | | | | | |
| $Yb_2F_6$ | | | | | | | | | | |
| $n_d$ | 1.621 | 1.571 | 1.581 | 1.571 | 1.571 | 1.602 | 1.681 | 1.661 | 1.561 | 1.581 |
| D | 3.444 | 2.914 | 2.894 | 2.854 | 2.744 | 3.077 | 3.054 | 4.084 | 3.104 | 3.074 |
| $F_o$ | 6.1 | 5.5 | 4.7 | 4.9 | 4.0 | 4.9 | 2.7 | 7.1 | 8.3 | 6.1 |

| | Example No. | | | | | | | | | |
|---|---|---|---|---|---|---|---|---|---|---|
| | 21 | 22 | 23 | 24 | 25 | 26 | 27 | 28 | 29 | 30 |
| $SiO_2$ | 88.1 | 88.1 | 92 | 92 | 92 | 92 | 92 | 92 | 92 | 92 |
| $Yb_2O_3$ | 0.1 | 0.1 | 0.1 | 0.1 | 0.1 | 0.1 | 0.1 | 0.1 | 2 | 2 |
| $ZrO_2$ | 1.9 | 1.9 | 3 | 3 | 3 | 3 | 3 | 3 | 3 | 3 |
| $Nb_2O_5$ | | | 4.9 | | | | | | 3 | |
| $Ta_2O_5$ | | | | 4.9 | | | | | | 3 |
| $HfO_2$ | | | | | 4.9 | | | | | |
| $WO_3$ | | | | | | 4.9 | | | | |
| $La_2O_3$ | 9.9 | | | | | | 4.9 | | | |
| $Y_2O_3$ | | 9.9 | | | | | | 4.9 | | |
| $La_2F_6$ | | | | | | | | | | |
| $Yb_2F_6$ | | | | | | | | | | |
| $n_d$ | 1.581 | 1.571 | 1.573 | 1.564 | 1.51 | 1.522 | 1.519 | 1.514 | 1.553 | 1.549 |
| D | 2.984 | 2.764 | 2.547 | 3.097 | 2.547 | 2.537 | 2.487 | 2.377 | 2.597 | 2.937 |
| $F_o$ | 5.4 | 4.1 | 2.2 | 7.8 | 13.0 | 6.4 | 5.8 | 3.2 | 3.5 | 8.1 |

| | Example No. | | | | | | | |
|---|---|---|---|---|---|---|---|---|
| | 31 | 32 | 33 | 34 | 35 | 36 | 37 | 38 |
| $SiO_2$ | 92 | 92 | 92 | 92 | 92 | 93.8 | 93.8 | 92 |
| $Yb_2O_3$ | 2 | 2 | 2 | 2 | 2 | | | |

TABLE 1-continued

| Compositions of the X-ray opaque glass in mol % | | | | | | | | |
|---|---|---|---|---|---|---|---|---|
| $ZrO_2$ | 3 | 3 | 3 | 3 | 3 | 4.2 | 6.2 | 8 |
| $Nb_2O_5$ | | | | | | | | |
| $Ta_2O_5$ | | | | | | | | |
| $HfO_2$ | 3 | | | | | | | |
| $WO_3$ | | 3 | | | | | | |
| $La_2O_3$ | | | 3 | | | | | |
| $Y_2O_3$ | | | | 3 | | | | |
| $La_2F_6$ | | | | | 3 | | | |
| $Yb_2F_6$ | | | | | | 2 | | |
| $n_d$ | 1.515 | 1.523 | 1.521 | 1.518 | 1.518 | 1.501 | 1.498 | 1.513 |
| D | 2.607 | 2.597 | 2.567 | 2.507 | 2.605 | 2.419 | 2.297 | 2.357 |
| $F_o$ | 11.5 | 7.7 | 7.5 | 6.7 | 9.8 | 22.7 | | |

The invention claimed is:

1. An X-ray opaque glass with a composition, in mol %, consisting of:

| | |
|---|---|
| $SiO_2$ | 75-92 |
| $Yb_2O_3$ | 0.1-25 |
| $ZrO_2$ | 0-24.9. |

2. The X-ray opaque glass as defined in claim 1, wherein said $Yb_2O_3$ is present in an amount of from 0.5 to 15 mol % and said $ZrO_2$ is present in an amount of from 0.5 to 15 mol %.

3. The X-ray opaque glass as defined in claim 1, wherein said $Yb_2O_3$ is present in an amount of from 1 to 15 mol %, and said $ZrO_2$ is present in an amount of from 1 to 15 mol %.

4. A process of making a glass with a composition as defined in claim 1, said process comprising the steps of:
   a) preparing a glass batch from raw material ingredients;
   b) charging the glass batch into a melting vessel; and
   c) melting the glass batch in the melting vessel at a melting temperature of at least 1500° C.;
   whereby said glass is formed with said composition as defined in claim 1.

5. The process as defined in claim 4, wherein said melting temperature is at least 1600° C.

6. The process as defined in claim 4, wherein said melting vessel comprises solid iridium and/or an alloy containing iridium.

7. The process as defined in claim 4, further comprising introducing high-frequency electromagnetic radiation into said glass batch in order to aid the melting of the glass batch.

8. The process as defined in claim 7, wherein said high-frequency electromagnetic radiation has frequencies from 50 kHz to 2 MHz.

9. The process as defined in claim 4, wherein at least one of said raw material ingredients is present in the glass batch in the form of a nanoscale powder prior to the charging of the glass batch into the melting vessel.

10. The process as defined in claim 4, wherein at least one of said raw material ingredients is present in the glass batch in the form of a nanoscale powder dispersed and/or dissolved in a solvent, and further comprising introducing said glass batch into a mold and drying said raw material ingredients to form a green body.

11. The process as defined in claim 10, wherein said drying of said raw material ingredients that were dissolved and/or dispersed and introduced into said mold is carried out with the aid of microwave radiation.

12. The process as defined in claim 11, wherein said mold comprises a non-wetting material.

13. The process as defined in claim 12, wherein said non-wetting material is a fluoropolymer.

14. The process as defined in claim 10, wherein said green body is a single entity or in milled form.

15. The process as defined in claim 10, further comprising sintering said green body.

16. The process as defined in claim 15, further comprising at least partially using waste heat produced in said melting for said sintering.

17. The process as defined in claim 10, further comprising milling, dissolving and/or dispersing said green body and subsequently drying to form a compact body.

18. The process as defined in claim 17, further comprising sintering said compact body.

19. The process as defined in claim 18, further comprising at least partially using waste heat produced in said melting for said sintering.

20. The process as defined in claim 17, wherein said green body is dissolved and/or suspended in an alkali metal lye or aqueous ammonia.

21. The process as defined in claim 10, wherein said solvent is an alkali metal lye or aqueous ammonia.

22. A dental glass consisting of the glass as defined in claim 1.

23. A filler for a composite used for dental restoration, consisting of the glass as defined in claim 1.

24. A composite used for dental restoration, said composite consisting of an epoxy resin and the glass as defined in claim 1, wherein said glass acts as a filler in the composite.

25. A dental composition comprising the X-ray opaque glass as defined in claim 1.

26. A substrate glass for a photovoltaic device, said substrate glass consisting of the glass as defined in claim 1.

27. A lamp glass consisting of the glass as defined in claim 1.

28. A target material for a plasma vapor deposition process, consisting of the glass as defined in claim 1.

29. A glass fiber consisting of the glass as defined in claim 1.

30. A glass fiber for reinforcing concrete, said glass fiber consisting of the glass as defined in claim 1.

31. A X-ray opaque glass with a composition, in mol %, consisting of:

| | |
|---|---|
| $SiO_2$ | 75-92 |
| $Yb_2O_3$ | 0.1-25 |
| $ZrO_2$ | 0-24.9 |
| $WO_3$ | 0-24.9 |

-continued

| | |
|---|---|
| La$_2$O$_3$ | 0-24.9 |
| Nb$_2$O$_5$ | 0-24.9 |
| HfO$_2$ | 0-24.9 |
| Ta$_2$O$_5$ | 0-24.9 |
| Gd$_2$O$_3$ | 0-24.9 |
| Lu$_2$O$_3$ | 0-24.9 |
| Sc$_2$O$_3$ | 0-24.9 |
| Y$_2$O$_3$ | 0-24.9 |
| F$_2$ | 0-5. |

32. The X-ray opaque glass as defined in claim 31, containing at most five oxide ingredients.

33. The X-ray opaque glass as defined in claim 31, containing at most four oxide ingredients.

34. A X-ray opaque glass with a composition, in mol %, consisting of:

| | |
|---|---|
| SiO$_2$ | 75-92 |
| Yb$_2$O$_3$ | 0.1-25 |
| ZrO$_2$ | 0-24.9 |
| Li$_2$O | 0-<10 |
| Na$_2$O | 0-<10 |
| K$_2$O | 0-<10, | wherein $\Sigma$Li$_2$O+Na$_2$O+K$_2$O is from 0 to <10 mol %.

35. A X-ray opaque glass with a composition, in mol %, consisting of:

| | |
|---|---|
| SiO$_2$ | 75-92 |
| Yb$_2$O$_3$ | 0.1-25 |
| ZrO$_2$ | 0-24.9 |
| MgO | 0-10 |
| CaO | 0-10 |
| SrO | 0-10 |
| BaO | 0-10 |
| ZnO | 0-10, | wherein $\Sigma$MgO+CaO+SrO+BaO is from 0 to <10 mol %.

36. A X-ray opaque glass with a composition, in mol %, consisting of:

| | |
|---|---|
| SiO$_2$ | 75-92 |
| Yb$_2$O$_3$ | 0.1-25 |
| ZrO$_2$ | 0-24.9 |
| TiO$_2$ | 0-10 |
| GeO$_2$ | 0-10 |
| P$_2$O$_5$ | 0-10, | wherein $\Sigma$TiO$_2$+GeO$_2$+P$_2$O$_5$ is from 0 to <15 mol %.

37. A glass powder with a mean grain size of up to 20 μm and a composition, in mol %, consisting of:

| | |
|---|---|
| SiO$_2$ | 75-92 |
| Yb$_2$O$_3$ | 0.1-25 |
| ZrO$_2$ | 0-24.9. |

38. The glass powder as defined in claim 37, and having a silanized surface.

39. A X-ray opaque glass with a composition, in mol %, consisting of:

| | |
|---|---|
| SiO$_2$ | 75-92 |
| Yb$_2$O$_3$ | 0.1-25 |
| ZrO$_2$ | 0-24.9 |
| WO$_3$ | 0-24.9 |
| La$_2$O$_3$ | 0-24.9 |
| Nb$_2$O$_5$ | 0-24.9 |
| HfO$_2$ | 0-24.9 |
| Ta$_2$O$_5$ | 0-24.9 |
| Gd$_2$O$_3$ | 0-24.9 |
| Lu$_2$O$_3$ | 0-24.9 |
| Sc$_2$O$_3$ | 0-24.9 |
| Y$_2$O$_3$ | 0-24.9 |
| TiO$_2$ | 0-10 |
| GeO$_2$ | 0-10 |
| P$_2$O$_5$ | 0-10 |
| Li$_2$O | 0-<10 |
| Na$_2$O | 0-<10 |
| K$_2$O | 0-<10 |
| MgO | 0-10 |
| CaO | 0-10 |
| SrO | 0-10 |
| BaO | 0-10 |
| ZnO | 0-10 |
| F$_2$ | 0-5; | wherein $\Sigma$TiO$_2$+GeO$_2$+P$_2$O$_5$ is from 0 to <15 mol %, $\Sigma$Li$_2$O+Na$_2$O+K$_2$O is from 0 to <10 mol %, and $\Sigma$MgO+CaO+SrO+BaO is from 0 to <10 mol %.

40. The X-ray opaque glass as defined in claim 39, in the form of a glass powder with a mean grain size of 0.2 μm to 20 μm.

41. The X-ray opaque glass as defined in claim 40, wherein said glass powder has a silanized surface.

42. A X-ray opaque glass with a composition, in mol %, consisting of:

| | |
|---|---|
| SiO$_2$ | 75-88.1 |
| Yb$_2$O$_3$ | 0.1-25 |
| ZrO$_2$ | 0-24.9 |
| WO$_3$ | 0-24.9 |
| La$_2$O$_3$ | 0-24.9 |
| Nb$_2$O$_5$ | 0-24.9 |
| HfO$_2$ | 0-24.9 |
| Ta$_2$O$_5$ | 0-24.9 |
| Gd$_2$O$_3$ | 0-24.9 |
| Lu$_2$O$_3$ | 0-24.9 |
| Sc$_2$O$_3$ | 0-24.9 |
| Y$_2$O$_3$ | 0-24.9. |

43. A X-ray opaque glass with a composition, in mol %, consisting of:

| | |
|---|---|
| SiO$_2$ | 75-88.1 |
| Yb$_2$O$_3$ | 0.1-25 |
| ZrO$_2$ | 0-24.9. |

44. A glass powder with a mean grain size of up to 20 μm and a composition, in mol %, consisting of:

| | |
|---|---|
| SiO$_2$ | 75-88.1 |
| Yb$_2$O$_3$ | 0.1-25 |
| ZrO$_2$ | 0-24.9. |

* * * * *